United States Patent [19]

Powell et al.

[11] Patent Number: 4,657,900

[45] Date of Patent: Apr. 14, 1987

[54] PHARMACEUTICAL ARTICLE OF MANUFACTURE COMPRISING A BISULFITE STABILIZED AQUEOUS SOLUTION OF 5-AMINOSALICYLIC ACID AND METHOD

[75] Inventors: David R. Powell; Vithal K. Patel, both of Baudette, Minn.

[73] Assignee: Rowell Laboratories, Baudette, Minn.

[21] Appl. No.: 717,062

[22] Filed: Mar. 28, 1985

Related U.S. Application Data

[63] Continuation-in-part of Ser. No. 536,428, Sep. 27, 1983, abandoned.

[51] Int. Cl.$^4$ .......................................... A61K 31/615
[52] U.S. Cl. .................................... 514/166; 514/973
[58] Field of Search ............................... 514/166, 973

[56] References Cited

U.S. PATENT DOCUMENTS

| | | | |
|---|---|---|---|
| 2,939,818 | 6/1960 | Berger | 424/175 |
| 3,230,143 | 1/1966 | Marcus | 424/175 |
| 3,777,019 | 12/1973 | Levin | 424/175 |
| 4,071,620 | 1/1978 | Sklar | 424/175 |
| 4,406,888 | 9/1983 | Aquiar et al. | 424/175 |
| 4,440,763 | 4/1984 | Lover | 514/166 |

OTHER PUBLICATIONS

Husa's—"Pharmaceutical Dispensing", Martin, Sixth ed., Mack Pub. Co., Easton, Penna. (1966).

*Primary Examiner*—Frederick E. Waddell
*Attorney, Agent, or Firm*—Millen & White

[57] ABSTRACT

An aqueous suspension of pure 5-aminosalicylic acid adapted for rectal administration is rendered storage stable against color formation by storing the suspension in a single dose polyethylene bottle adapted for rectal administration of the suspension, in a substantially oxygen-free atmosphere and in the presence dissolved therein of up to about 0.25% of bisulfite and protecting the suspension from exposure to atmospheric oxygen during storage by sealing the plastic bottle, in a substantially oxygen-free atmosphere, in a plastic pouch having a low oxygen transmission rate.

20 Claims, No Drawings

PHARMACEUTICAL ARTICLE OF MANUFACTURE COMPRISING A BISULFITE STABILIZED AQUEOUS SOLUTION OF 5-AMINOSALICYLIC ACID AND METHOD

This is a continuation-in-part of application Ser. No. 536,428, filed Sept. 27, 1983, now abandoned.

BACKGROUND OF THE INVENTION

This invention relates to an article of manufacture comprising a stabilized aqueous solution of pure 5-aminosalicylic acid (5-ASA).

5-ASA is a position isomer of the well known antitubercular agent p-aminosalicylic acid (4-ASA). However, it has completely different chemical and therapeutic properties. One of the most difficult chemical problems of 5-ASA is its lack of stability in aqueous solutions or suspensions.

Since it has been discovered to be the active moiety of sulfasalazine (used to treat ulcerative colitis), 5-ASA has been the focal point of numerous clinical investigations. Dosage forms for these investigations included powders for reconstitution, short-lived suspensions (7–14 days), wax suppositories and oral tablets. Investigators have recognized that 5-ASA is highly degradable in aqueous systems.

Aqueous solutions of 5-ASA are so unstable that heretofore they have been effectively eliminated as a commercially viable form for rectal administration. Attempts to protect them from decomposition upon prolonged storage, e.g., by storing them in sealed glass containers or under refrigeration have proved futile. Non-aqueous rectal forms of 5-ASA were not a viable alternative because of concerns that they might be less effective than aqueous forms and 5-ASA is substantially ineffective orally to treat diseases of the colon, such as ulcerative colitis. Therefore, the prior art approach to the problem has been to develop a pro-drug which will form 5-ASA in situ in the colon.

In its sulfasalazine pro-drug form, 5-ASA is chemically stabilized by the azo group linking it to sulfapyridine. When sulfasalazine reaches the colon by either oral or rectal administration, the colonic bacteria reduce the azo linkage, freeing 5-ASA and sulfapyridine. Sulfapyridine has no therapeutic benefit towards ulcerative colitis but nevertheless is responsible for dose-related side-effects. Numerous other pro-drugs have been considered wherein 5-ASA is azo-linked to an innocuous substance or a second molecule of 5-ASA. This constitutes a method of promoting chemical stability but may result in some of the disadvantages associated with sulfasalazine. For example, azo forms of 5-ASA must reach the colon to be metabolized and bioavailability is questionable since metabolism may not be complete, especially in patients on antibiotics.

Some physicians have supplied 5-ASA to the patient in dry form, to be made up by the patient with an aqueous solution immediately prior to rectal administration, or in small batches as aqueous solutions which would be used up by the patient before significant color formation occured. Neither of these approaches were completely satisfactory from a physician-patient point of view.

We therefore investigated the possibility of producing an aqueous solution of 5-ASA which was stabilized against decomposition and color formation for the prolonged storage period required of a commercial pharmaceutical product. In doing so, it was found that unless the starting 5-ASA is very pure, it is virtually impossible to prevent its decomposition, apparently because of the auto-catalytic effects of the impurities on decomposition and color formation. Therefore, the first step in achieving a storage-stable 5-ASA was the development of an acceptable purification process, since the commercially available 5-ASA (in production lots) is a technical grade.

We found that pure 5-ASA suitable for use in the compositions of this invention can be produced by decolorizing an acidic concentrated solution thereof with activated charcoal. In contradistinction, its position isomer, 4-ASA, is purified via its sodium salt. See, e.g., U.S. Pat. No. 2,658,073 and 2,844,625. However, 5-ASA is unstable in alkaline solutions and its purification via its sodium salt is therefore not feasible.

The next step in our investigation was finding a way to prevent the decomposition of and color formation in initially colorless solutions of substantially pure 5-ASA. In doing so, we found that bisulfite would inhibit decomposition of and initial color formation in such solutions. This was surprising because even solutions of 5-ASA which had been carefully purged with nitrogen developed color upon long term storage, after packaging using conventional pharmaceutical equipment. Therefore, an anti-oxidant seemed inappropriate as a stabilizing agent.

Sulfite has been used in the prior art as stabilizers or antioxidants for a wide variety of drugs representing broad chemical and pharmacological classes. See Louis C. Schroeter, "Sulfur Dioxide. Applications in Foods, Beverages and Pharmaceuticals", pp. 228–265, esp. 257–261 and cases cited therein (Pergamon Press, 1966).

U.S. Pat. No. 2,647,843 incorrectly teaches that aqueous solutions of 4-ASA are stabilized against color formation resulting from oxidation upon storage with sulfites or bisulfites. In fact, 4-ASA is decomposed by decarboxylation at acid pH, not by oxidation as is 5-ASA. Early researchers believed that because bisulfite prevented color formation, it stabilized 4-ASA solutions. This later was proved to be incorrect. Actually, only the formation of the azoxy-benzene chromagen was inhibited (Pharm. Sci., 60, No. 12, Dec. 1977, pp. 1886-7). It is alkaline pHs, not bisulfite, which prevents decomposition of the 4-ASA.

Because bisulfite alone did not prevent color formation in the 5-ASA solutions upon prolonged storage, we investigated the use of a combination of bisulfite and the chelating agent ethylenediaminetetraacetic acid, in the event the delayed color formation was due to the presence in the solution of trace amounts of heavy metals which are known to catalyze color-forming reactions.

The use of the combination of sodium bisulfite (antioxidant) and the disodium salt of EDTA (chelating agent) to stabilize injectable solutions of chlorpromazine hydrochloride solution in disposable cartridges is claimed in U.S. Pat. No. 3,777,019. Color formation in such solutions was due to the oxygen intrusibility of the disposable cartridges in which the chlorpromazine solution was marketed, rather than the intrinsic instability of the chlorpromazine, which is storage stable in flame-sealed all-glass ampuls or rubber-closured glass vials. Martindale, *The Extra Pharmacopedia*, 28th Ed., pp. 1291-2 (The Pharmaceutical Press, London, 1982) states that sodium metabisulfite is widely used as an antioxidant at concentrations ranging from 0.01% to 1% in solutions (usually in acid preparations with sodium sulfite preferred for alkaline preparations), especially those that contain drugs which are readily oxidized to form highly colored products and that a chelating agent, such as sodium edetate, is sometimes added thereto to remove heavy metal ions which often catalyze auto-oxidation reactions.

The decomposition of solutions of 5-ASA appears not to be metal ion initiated, since EDTA alone is completely ineffectual in inhibiting that decomposition whereas the bisulfite alone ordinarily inhibits color formation, except upon prolonged storage. In contradistinction to 4-ASA, 5-ASA decomposes as a result of oxygen attack on the amino group, yielding 2,5-dihydroxybenzoic acid as a major decomposition product. The mechanism for color formation is not known. However, intense color formation can occur even with only slight decomposition of the 5-ASA precentage-wise.

We ultimately found that EDTA did not improve the long term protection against color formation in aqueous solutions of 5-ASA achieved with bisulfite alone. Instead, paradoxically the bisulfite itself, at least in amounts we initially employed, was responsible for the color formation upon long terms storage, even though it did prevent loss of assay and short term (within 30 days) color formation.

Contrary to popular belief, we found that the decomposition of and color formation therein upon short term storage in initially colorless acid aqueous solutions of substantially pure 5-ASA is not due to the reaction of the 5-ASA with the water. Instead, it is due to the trace amount of atmospheric oxygen which is present in the solution after conventional pharmaceutical processing and packaging, even after nitrogen purging of the free space of the container in which the 5-ASA is packaged. We found that extremely small amounts of oxygen are capable of triggering such decomposition (loss of 5-ASA assay strength) and color formation (which can occur even with only negligible loss of 5-ASA assay strength).

In parent application Ser. No. 536,428, there are disclosed examples of aqueous colorless solutions of pure 5-ASA which were protected with 0.468% w/w of potassium metabisulfite against color formation for several months when stored in a sealed polyethylene squeeze bottle adapted for rectal administration of the 5-ASA. This amount of bisulfite was required because the solutions were exposed to atmospheric oxygen during storage as a result of being stored in plastic bottles having a substantial oxygen transmission rate. However, it was discovered that the solutions nevertheless ultimately developed color upon prolonged storage. We found that the amount of bisulfite required to ensure protection of 5-ASA against color formation resulting from reaction with the atmospheric oxygen transmitted thereto through the walls of the plastic bottle upon prolonged storage itself ultimately imparted an undesirable color change in the solution. The reason for such color change is not known other than it is due solely to the bisulfite in such solutions.

It is an object of this invention to provide means for preventing the color formation which occurs in aqueous 5-ASA solutions upon both short term and long term storage.

It is another object to provide pharmaceutical articles of manufacture which incorporate such means.

Upon further study of the specification and appended claims, further objects and advantages of this invention will become apparent to those skilled in the art.

SUMMARY OF THE INVENTION

In a process aspect, this invention relates to a method of protecting a substantially colorless aqueous solution of substantially pure 5-ASA from decomposition and color formation therein upon prolonged storage, which comprises the steps of:

(a) maintaining the solution during storage in the presence dissolved therein of an amount of bisulfite effective only to protect the 5-ASA against decomposition and color formation resulting from reaction of the 5-ASA with a trace amount of atmospheric oxygen present prior to storage but ineffective to protect against atmospheric oxygen transmitted to the solution during storage;

(b) storing the solution in a sealed container which contains therein no more than a trace amount of atmospheric oxygen; and (c) protecting the solution from contact with atmospheric oxygen during storage.

In any article of manufacture aspect, this invention relates to an article comprising:

(a) a first sealed container, adapted for storing aqueous liquids, substantially free of atmospheric oxygen and containing therein (b) a stable suspension adapted for rectal administration of substantially pure 5-aminosalicylic acid in a saturated, substantially colorless aqueous solution of 5-aminosalicylic acid of pharmaceutical grade purity having a pH of from about 3 to 5 and rendered resistant to color formation upon storage by the presence dissolved therein at a concentration of up to about 0.25% w/w, of an amount of bisulfite effective to stabilize the solution against color formation and degradation of the 5-aminosalicylic acid by the reaction with any trace amount of oxygen in the solution or the container; and;

(c) a second sealed container containing the first container stored therein in a substantially oxygen-free atmosphere, and comprising an oxygen barrier effective to prevent transmission into the interior of the second container upon prolonged storage of atmospheric oxygen in an amount sufficient to exhaust the bisulfite dissolved in the solution contained in the first container.

In a preferred article of manufacture aspect, the first container is a pharmaceutical product adapted for rectal administration of the stable suspension of substantially pure 5-ASA contained therein.

DETAILED DISCUSSION

The present invention is based on our discovery that under very specific conditions aqueous solutions of 5-ASA can be stabilized against both decomposition and color formation during prolonged storage.

The first requirement for the stabilization of a 5-ASA solutions upon prolonged storage is that the starting 5-ASA must be substantially pure and substantially colorless. Every colorless 5-ASA, if impure, will rapidly develop color as an aqueous solution.

The next requirement is that decomposition (loss of assay strength) and rapid formation of color in the 5-ASA solution, i.e., within about 30 days be inhibited with bisulfite. In order for the bisulfite to be effective as a stabilizer, the 5-ASA solution must be acidic, i.e., with a pH below about 6, e.g., about 3 to 5, preferably about 4.5. In contradistinction, 4-ASA solutions are stabilized against color formation only at alkaline pHs. See Martindale, supra, p. 1568. 50% of the 4-ASA decomposes in 10 weeks at pH 5 and in 10 days at pH 4. A. Angren, *J. Pharm. Pharmac.*, Vol. 7, p. 549.

The next requirement is that the concentration of bisulfite employed to do so must be small, i.e., present therein at a concentration of up to about 0.25% w/w, preferably about 0.05 to 0.2% w/w and more preferably about 0.1 to 0.2% by weight. Paradoxically, higher concentrations of bisulfite will themselves ultimately trigger color formation in 5-ASA solutions upon prolonged storage.

The next requirement is that the thus-stabilized solution be protected from exposure to any significant amount of atmospheric oxygen upon prolonged storage. The low concentrations of bisulfite which are effective to inhibit decomposition of the 5-ASA and color formation of solutions thereof resulting from the presence initially of a trace amount of atmospheric oxygen in the solution and/or the container in which the solution is stored is incapable of preventing color formation in an aqueous solution of 5-ASA which is exposed to a significant amount of atmospheric oxygen during storage. Such exposure can easily occur because ordinarily the 5-ASA solution is stored in a plastic container adapted for rectal administration, e.g., a collapsible bottle formed of low density polyethylene. Such containers have a high oxygen transmission rate and the oxygen transmitted into the solution upon prolonged storage is sufficient to consume all of the bisulfite, thereby permitting oxygen-mediated color to develop. Conversely, higher concentrations of bisulfite will themselves generate color in the solution upon prolonged storage. Therefore bisulfite is effective to prevent color formation in aqueous solutions of 5-ASA upon prolonged storage only if the bisulfite stabilized solution is stored in a container which transmits little or no atmospheric oxygen through the walls thereof. This problem can be solved by employing an amount of bisulfite effective to protect the solution only against immediate color formation and packaging the solution in a container which transmits little or no atmospheric oxygen through its walls.

Purification of 5-ASA

The starting 5-ASA employed in the purification process of this invention is conventional commercially available technical grade 5-ASA, which forms visibly highly colored aqueous solutions. The substantially pure 5-ASA produced by this invention asays at least 99%, preferably at least 99.5%. It is essentially colorless, i.e., 1.0% aqueous solution in 1N HCl thereof has a color extinction value of less than 0.05 at wavelength range of 380 nm to 700 nm.

In the first step of the purification process, the starting 5-ASA is dissolved in an amount of a dilute aqueous pharmaceutically acceptable strong mineral or organic acid, e.g., HCl, $H_2SO_4$, $H_3PO_4$, $H_2SO_3$, or acetic acid, preferably of a concentration of about 1.0 N to about 4.0 N, preferably about 2 N to 4 N, to form a substantially saturated solution, e.g., within at least 1% and preferably at least 5% of saturation, the acid being sufficiently concentrated to produce a solution of the 5-ASA having a pH of less than about 2.5, preferably from about 0.5–2.5. This step can be conducted at any suitable temperature, e.g., from about 20°–80° C. A temperature of about 60°–80° C. is preferred because at lower temperatures, the yield of purified 5-ASA drops substantially and at higher temperatures, special precautions must be employed to avoid decomposing the 5-ASA, e.g., by conducting the step in the absence of light and atmospheric oxygen and/or in the presence of an antioxidant and optionally also a chelating agent which is operative at acidic pHs. Desirably, this step and the decolorization and separation steps which follow are conducted in the presence of a bisulfite or other antioxidant, to ensure that color by-products or their precursors do not develop.

In the next step of the process, the acidic solution of starting 5-ASA is decolorized in any conventional manner. Activated charcoal is very efficient, e.g., in weight ratios to the 5-ASA in solution from about 0.25–1.0, and is preferred. The decolorization step can be conducted at the same temperatures as in the preceding step. A temperature of about 60°–80° C. is preferred for the same reasons. Optionally and preferably, especially if the 5-ASA is not promptly precipitated from the decolorized solution, bisulfite is added thereto, either prior to or after the decolorization step, e.g., at a concentration of about 0.01-2% by weight.

In the next step of the process, the thus-purified 5-ASA is precipitated from the decolorized solution thereof by raising the pH thereof to 3.5–4.0, e.g., with a pharmaceutical base such as NaOH, KOH, $Na_2CO_3$, $NaHCO_3$, $NH_3$, $Na_3PO_4$, which will neutralize a portion of the acid without forming a precipitate therewith. In this step, the mixture is preferably at or is cooled to about room temperature or below, e.g., 0°–5° C., before the precipitated 5-ASA is separated therefrom. At pH 1.8, the 5-ASA begins to precipitate and continues to precipitate as more base is added until a pH of 4.5 is reached, at which pH the base forms a soluble salt with the base and no further 5-ASA precipitates.

In the next step of the process, the precipitated 5-ASA is separated from the mother liquor, e.g., by filtration or centrifugation, followed by washing to remove residual mother liquor adhering to the separated 5-ASA, e.g., until the wash water passes the Sodium and Chloride USP tests. The wash water can be discarded or mixed with the mother liquor, which preferably is used to form the starting dilute acid employed with another batch of starting 5-ASA.

In the final step of the process, the thus-purified 5-ASA is conventionally dried, e.g., in a vacuum oven at 75°–90° C. To facilitate drying, the wet 5-ASA can first be washed with USP ethyl alcohol, e.g., 2–10 ml/g., preferably successively in several portions. The alcohol can be discarded or dewatered for reuse.

The thus-purified 5-ASA is substantially pure, i.e., at least 99%, preferably at least 99.5% purity. It forms substantially colorless solutions, i.e., a saturated aqueous solution thereof looks like water. It is storage stable under a variety of conditions (except as aqueous solutions) but is preferably stored in an anhydrous state in a $N_2$ gas flushed and sealed container.

Stabilized solutions of 5-ASA

According to this invention, substantially colorless aqueous solutions of substantially pure (pharmaceutical grade) 5-ASA are stabilized against color formation upon prolonged storage, viz., for at least several months, e.g., at least 12 and easily 24 or more, by (a) dissolving therein an amount of bisulfite effective to protect the 5-ASA against reaction with at most a trace amount of oxygen, i.e., in a concentration therein from about 0.01%–25% by weight, preferably about 0.05%–0.2% and most preferably about 0.1%–0.2% by weight; b) packaging the solution in a sealed container which is substantially free of atmospheric oxygen; and (c) protecting the solution from exposure to atmospheric oxygen while maintained in the sealed container.

Although the bisulfite is effective in preventing color formation in substantially oxygen-free 5-ASA solutions over prolonged periods of time, e.g., several months or more, it is ineffective to protect against color formation if the solution is exposed to atmospheric oxygen during prolonged storage because the amount of bisulfite required to prevent reaction with atmospheric oxygen transmitted through the walls of the container will itself impart color to the solution upon prolonged storage.

If the starting 5-ASA contains trace amounts of heavy metals, color formation as a result of their presence can be avoided by employing the bisulfite in combination with EDTA.

The bisulfite and EDTA can be supplied in any convenient form, e.g., as a soluble salt thereof, such as an alkali metal salt, and can be dissolved in the water used to form the 5-ASA solutions prior to, preferably concurrently with or less desirably after dissolving the 5-ASA therein. In the latter case, the 5-ASA solution preferably is protected against light and oxygen until the bisulfite and EDTA is dissolved therein.

The 5-ASA employed to produce the stable solutions is pharmaceutical grade and forms initially colorless aqueous solutions. Because the stabilized solutions are employed as pharmaceutical products, the bisulfite, EDTA and water employed to produce them also are preferably of USP grade. The 5-ASA can be present in the stabilized solutions at any desired concentration but preferably it is at saturation.

Aqueous 5-ASA Pharmaceutical Products

Because 5-ASA is only sparingly soluble in water at pHs from about 3–5, e.g., about 0.12% to 0.15%, and because the amount of 5-ASA per unit dosage employed in the treatment of colitis and other abnormalities of the colon, would require the administration of a huge volume of a saturated solution of 5-ASA, the 5-ASA preferably is administered as an aqueous slurry containing a large amount of undissolved 5-ASA, as described hereinafter.

The pharmaceutical articles of manufacture of this invention comprise a stable suspension or slurry of pharmaceutical grade 5-ASA in a stabilized colorless aqueous solution of pharmaceutical grade 5-ASA as defined hereinbefore, i.e., the slurry preferably contains from about 1.0–25.0% preferably about 1.5–10% by weight, of 5-ASA. Such suspensions have an off-white to pinkish-tan appearance due to the undissolved 5-ASA. However, the same 5-ASA forms colorless solutions.

In addition to containing a stabilizing amount of bisulfite and optionally also EDTA, the slurry preferably contains an amount of suspending agent effective to maintain the undissolved 5-ASA suspended therein. Viscosity raising agents conventionally employed in aqueous pharmaceutical solutions, e.g., a natural or synthetic gum, e.g., xanthan gum or gum tragacanth, in amounts which increase the viscosity of the slurry to about 100–600 cps, preferably about 400 cps, are effective, e.g., at concentrations from about 0.1%–0.25%. To prevent caking of the 5-ASA, a floculating agent, e.g., a water gellable cross-linked polyacrylic acid, is desirably also included, e.g., at a concentration of about 0.05%–0.15%.

The pH of the pharmaceutical products is acidic, preferably about 3 to 5, most preferably about 4.5. When the slurry contains a floculating agent, the 5-ASA solution preferably contains a buffer, e.g., potassium acetate, effective to maintain the pH of the solution at about 4. At this pH the solution is less stable and more care must be exercised to ensure that the solution is never exposed to more than at most a trace amount of oxygen.

The pharmaceutical products of this invention preferably also contain a conventional bacteriostat, e.g., sodium benzoate, to ensure against bacterial contamination. Other conventional excipients, e.g., opacifying agent, colorant and perfume can be present as well as other active ingredients useful for concurrent therapy along with the 5-ASA, e.g., steroids, such a hydrocortisone or a synthetic anti-inflammatory steroid.

The 5-ASA solution should be stored in an atmosphere which contains no more than a trace of free oxygen, i.e., it is substantially oxygen-free. The atmosphere above it in the container in which the solution is stored should contain no more than about 2,500 ppm and preferably less than about 1,000 ppm free oxygen, e.g., by purging the atmosphere with oxygen-free nitrogen and/or by placing the solution under a vacuum and then returning the solution to atmospheric pressure in the container in which the solution is to be stored with oxygen-free nitrogen and promptly thereafter sealing the container.

5-ASA Articles of Manufacture

The substantially oxygen-free 5-ASA solution can be protected from exposure to atmospheric oxygen during prolonged storage in a variety of ways, e.g., by storing the 5-ASA solution in a container whose walls do not easily transmit oxygen therethrough, e.g., a glass container, by storing the 5-ASA solution in a container whose walls do transmit atmospheric oxygen but which in turn is stored in a substantially oxygen-free container. The latter is preferred because the 5-ASA solution is most conventionally administered from a collapsible plastic bottle formed of low density polyethylene, which has a relatively high oxygen transmission rate.

In its preferred article of manufacture form, the pharmaceutical products of this invention comprise a single unit dosage amount of a 5-ASA slurry of this invention in a sealed container adapted for rectal administration of the 5-ASA solution, e.g., a disposable collapsible plastic, e.g., polyethylene or polypropylene, enema bottle with a lubricated dispensing tip, covered with a sealing cap, adapted for insertion into the rectum when the cap is removed and dispensing the contents of the bottle into the lower colon when the bottle is manually squeezed. An example of an otherwise identical (except for its contents) commercially available product is Rowell Laboratories, Inc. (Baudette, Minn.) Cortenema ® disposable unit-dose hydrocortisone retention enema, each unit of which contains 60 ml. of product. A comparable product of this invention contains 60 ml. of a slurry of 5-ASA of this invention. The solution is protected from exposure to a significant amount of atmospheric oxygen during storage by a sheet, film or foil forming a continuous wall around the container for the solution and having a substantially lower oxygen permeability than the walls of the container for the suspension, i.e., less than 0.5 cc-mil/100 Inch$^2$/24 hours/Atmospheric conditions/23° C., and preferably less than about 0.25. This sheet, foil or film can be bonded directly to the outer wall of the container for the 5-ASA, thereby forming a laminate wall, or it can be in the form of a sealed pouch or package for the container, e.g., a glass bottle, a steel or aluminum can or an aluminum foil-cardboard laminate can. Any free space in the sealed pouch or package will be provided substantially oxygen free. The substantially oxygen impermeable foil or film can be formed from a single material, e.g, aluminum foil, or from a plurality of materials in the form of a laminate, e.g., a heat sealable polyester film/aluminum foil/polyethylene film laminate. Other films with low oxygen permeability are Dow Chemical Company's High Barrier Saran ® Warp and Allied Corporation Capran EBO.

Contemplated equivalents of the bisulfite employed in this invention are other physiologically acceptable, water soluble antioxidants which collectively inhibit the formation of colored products in 5-ASA solutions on storage by reaction of the 5-ASA with atmospheric oxygen.

Reference is made herein to final products which comprise an aqueous solution of 5-ASA. Because the presence of undissolved 5-ASA in such solutions does not affect decomposition rates and color formation and because the contemplated commercial form of such products is such a suspension, the term "solution" as so used is intended to embrace such suspensions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

PREPARATION ONE

Purification of 5-ASA

Dissolve 100 g. of ca. 95% 5-ASA (Technical Grade) in 2,000 ml. of 2 N HCl (AR Grade) with heating to 60°-80° C. to facilitate rate of solution. Remove any undissolved material by filtering the hot solution through a suitable acid stable filtering medium (analytical filter paper). Add 20 g. of decolorizing activated charcoal (Darco G-60) to the tan colored hot filtrate and mix for 5 minutes while maintaining its temperature at about 60° C. Filter through a filtering medium as above (analytical filter paper) and cool the filtrate to 15°-20° C. Raise the pH thereof to 3.5-4.0 with about 560 ml. of high purity 28.6% (7.14 N) NaOH. At a pH of about 1.8 to 2.0, the 5-ASA beings to precipitate. When precipitation has completed, collect the precipitated 5-ASA by vacuum filtration. Retain the mother liquor and wash with U.S.P. water until the rinse is free of sodium and chloride and then with 2×200 ml. of anhydrous ethanol (SDA-3A) and dry the washed 5-ASA in a vacuum oven. Yield of 5-ASA which forms colorless aqueous solutions, about 95-97 g. (about 95% yield based on the 5-ASA content of the starting technical grade 5-ASA).

PREPARATION TWO

Purification of 5-ASA

Charge 1810 g. USP water into a 4 liter beaker and slowly add 196 g. sulfuric acid R.R. thereto while stirring. Heat to 60°-80° C. while stirring. Slowly add 100 g. (pure basis) Technical Grade (ca. 90-95% purity), 5-aminosalicylic acid to dissolve. Maintain temperature of the solution at 60°-80° C. Add 20 g. activated charcoal and stir for 5-30 minutes. Maintain temperature at 60°-80° C. and filter the charcoal suspension through analytical filter paper. Collect the filtrate, cool to 0°-5° C. Add and dissolve 0.5 g. sodium bisulfite USP therein. Dissolve 160 g. sodium hydroxide USP in 400 g. water USP, and cool the solution to 0.5° C. and slowly add to the 5-ASA solution while stirring to about pH 3.5, using a pH meter. Use additional 1 N sodium hydroxide solution if needed. Cool the resultant 5-ASA slurry to 0°-5° C. and separate the 5-ASA crystals from slurry using Buchner funnel and vacuum pump (or suitable vacuum filtering device). Discard filtrate and rinse the crystal bed with water USP at 2°-5° C. until the rinse is free of sulfate and sodium ions. Use vacuum to remove water from the crystal bed. Rinse the crystal bed with 300 g. alcohol SDA-3A. Use vacuum to remove alcohol from the crystal bed. Tray out the crystals and dry at 75°-90° C. (or with vacuum at 75°-90° C.) for 6-8 hours. Yield, based on the 5-ASA content of the starting technical grade 5-ASA, is 95%.

PREPARATION THREE

Stable Aqueous 5-ASA Suspensions

| Item | Ingredients | Example 1 Amount | Example 1 % w/w | Example 2 Amount | Example 2 % w/w |
|---|---|---|---|---|---|
| 1 | Water RODI | 20,000 g. | 80.0 | 18,750 g. | 75.0 |
| 2 | Sodium Benzoate | 25 g. | 0.10 | 25 g. | .10 |
| 3 | Carbopol 934P | 18.75 g. | 0.075 | 18.75 g. | 0.075 |
| 4 | Disodium EDTA | 25 g. | 0.10 | 25 g. | 0.10 |
| 5 | Potassium Metabisulfite 29.25 | 29.5 g.– 117 g. | 0.117– 0.468 | 29.25 g.– 117 g. | 0.117– 0.468 |
| 6 | Potassium Acetate | 102.5 g. | 0.41 | 102.5 g. | 0.41 |
| 7 | Xanthan Gum | 62.5 g. | 0.25 | 62.5 g. | 0.25 |
| 8 | 5-Aminosalicylic Acid | 425 g. | 1.70 | 2,550 g. | 10.2 |
| 9 | Water RODI | 4,000 g. | 16.0 | 3,200 g. | 12.8 |
| 10 | Water RODI, QS to 25,000 g. | 224 g. | 0.9 | 149 g. | 0.6 |

Charge the Item #1 water into a 10 gallon stainless steel tank and dissolve the sodium benzoate therein using Lightning Mixer. Add Carbopol ® 934P slowly while mixing until a lump-free dispersion of Carbopol ® is produced. Mix for one hour and set overnight at room temperature with tank covered lightly. Mill dispersion for 10 minute using 1 hp G&W mill and then set for 30 minutes to deaterate. Add and dissolve disodium EDTA, the selected amount of potassium metabisulfite and potassium acetate therein while stirring with a Lightning Mixer, and then add xanthan gum slowly while mixing until it dissolves. Charge Item #9 water into a 5 gallon stainless steel container. Add the selected amount of 5-aminosalicylic acid purified according to Preparation Two thereto and slurry using Lightning Mixer. Add the resulting slurry to the previously obtained dispersion and mix for 15 minutes. Bring to 25,000 grams with Item #10 water and mix for one hour. Strain product through a 40 mesh in-line strainer during filling operation.

EXAMPLE ONE

5-ASA Pharmaceutical Articles of Manufacture

Fill a suspension of Example 1 containing 1 g of 5-ASA per 60 cc. to a target weight of 60.2 g. into commercially available 60 ml. capacity single dosage collapsible white opaque low density polyethylene bottles with snap ring necks. Flush nitrogen gas in the bottle to displace head space air and cap each with a special snap-on lubricated rectal applicator covered with a press fitted removable protective plastic cap.

To provide a thus filled bottle with an oxygen barrier, insert the bottle into a polyester/aluminum foil/polyethylene laminate heat sealable 6½"×8" plastic pouch (Kapak Corporation, St. Louis Park, MN), flush the pouch with nitrogen and immediately heat seal the pouch.

The effects of (a) the presence or absence of the oxygen barrier and (b) the concentration of bisulfite in the suspension upon the decomposition of the 5-ASA and color formation in suspensions packaged as described above, after storage under various conditions of the Example 1 suspensions is shown in the Table below.

TABLE

| Test No. | Storage Conditions | % Bisulfite | % 5-ASA Assay | Degradation spots[4] | pH | Appearance |
|---|---|---|---|---|---|---|
| I | | | Initial | | | |
| (a) | | 0.0 | 104.3 | no | 5.39 | Light Tan[5] |
| (b) | | 0.117 | 101.8 | " | 5.32 | " |
| (c) | | 0.234 | 101.1 | " | 5.30 | " |
| (d) | | 0.351 | 98.6 | " | 5.29 | " |
| (e) | | 0.468 | 100.3 | " | 5.28 | " |
| II | 1 week, 60°, Oxygen Chamber[2], No O$_2$ Barrier | | | | | |
| (a) | | 0.0 | 76.5 | yes | 5.12 | Dark Brown |
| (b) | | 0.117 | 81.3 | " | 4.81 | " |
| (c) | | 0.234 | 88.3 | " | 4.62 | " |
| (d) | | 0.351 | 94.1 | " | 4.34 | " |
| (e) | | 0.468 | 100.6 | " | 4.00 | Light Brown[6] |
| III | 3 mos., 45°, exposed to atmosphere[3], No O$_2$ Barrier | | | | | |
| (a) | | 0.0 | 49.6 | yes | 4.84 | Dark Brown |
| (b) | | 0.117 | 65.2 | " | 4.46 | " |
| (c) | | 0.234 | 79.4 | " | 4.38 | " |
| (d) | | 0.351 | 88.5 | " | 4.20 | " |
| (e) | | 0.468 | 92.7 | " | 3.86 | " |
| IV | 6 mos., 37°, exposed to atmosphere[3], No O$_2$ Barrier | | | | | |
| (a) | | 0.0 | 62.5 | yes | 4.95 | Dark Brown |
| (b) | | 0.117 | 78.2 | " | 4.76 | " |
| (c) | | 0.234 | 87.7 | " | 4.52 | " |
| (d) | | 0.351 | 95.9 | " | 4.28 | " |
| (e) | | 0.468 | 98.5 | " | 3.90 | Light Brown[6] |
| V | 3 mos., 45°, foil pouch oxygen barrier | | | | | |
| (a) | | 0.0 | 94.6 | yes | | Brown |
| (b) | | 0.117 | 96.8 | no | | V. Sl. Brown[7] |
| (c) | | 0.234 | 96.02 | " | | " |
| (d) | | 0.351 | 100.6 | " | | Sl. Brown[8] |
| (e) | | 0.468 | 99.4 | " | | " |
| VI | 6 mos., 37°, foil pouch oxygen barrier | | | | | |
| (a) | | 0.0 | 99.6 | yes | 5.27 | Dark Brown |
| (b) | | 0.117 | 101.7 | no | 5.02 | unchanged[7] |
| (c) | | 0.234 | 96.1 | " | 4.83 | Sl. Yellow[8] |
| (d) | | 0.351 | 97.1 | " | 4.68 | " |
| (e) | | 0.468 | 99.1 | " | 4.57 | " |

[1] Before Storage;
[2] Pure Oxygen;
[3] In sealed polyethylene bottle only;
[4] Paper chromatography;
[5] Due solely to undissolved 5-ASA;
[6] Significantly colored;
[7] Not significantly different from initial color;
[8] Noticeably more colored than sample VIb.

The Test I samples (pre-storage) all exhibited a faint color from undissolved 5-ASA. The solution itself was colorless.

The Test II Samples established that at elevated temperatures (60° C.), substantial degradation (as evidenced by lowered assay values and appearance of degradation spots) of the 5-ASA occurs within a week if the 5-ASA suspension is not protected by 0.351% or 0.468% concentrations of the bisulfite. Moreover, substantial color development occurred even in those samples in which relatively little decomposition of the 5-ASA had occurred (Samples IIIc and IIId). Only 0.468% bisulfite protected against both decomposition and substantial color development.

The Test No. III and IV data confirm the limited protection against color development achieved with bisulfite when the 5-ASA solution thereof is exposed to atmospheric oxygen during storage. The Test No. V and VI data show that when the 5-ASA solution is protected from atmospheric oxygen during storage, both decomposition and color formation is inhibited with low concentrations of bisulfite whereas at higher concentrations the bisulfite is responsible for color changes on storage.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical article of manufacture comprising:
    (a) a first sealed container, adapted for storing aqueous liquids, substantially free of atmospheric oxygen;
    (b) contained in the first sealed container, a stable suspension adapted for rectal administration of substantially pure 5-aminosalicylic acid in a saturated, substantially colorless and substantially oxygen-free aqueous solution of 5-aminosalicylic acid of pharmaceutical grade purity having a pH of from about 3 to 5 and rendered resistant to color formation upon storage by the presence dissolved therein at a concentration of up to about 0.25% w/w, of an amount of bisulfite effective to stabilize the solution against color formation and degradation of the 5-aminosalicylic acid by the reaction with any trace amount of oxygen in the solution or the container; and;

(c) a second sealed container containing the first container stored therein in substantially oxygen-free atmosphere, and comprising an oxygen barrier effective to prevent transmission into the interior of the second container upon prolonged storage of atmospheric oxygen in an amount sufficient to exhaust the bisulfite dissolved in the solution contained in the first container.

2. An article according to claim 1 wherein the first container is a plastic bottle.

3. An article according to claim 1 wherein the first container is a single unit dosage disposable collapsible enema polyethylene bottle with a dispensing tip adapted for rectal administration of the 5-ASA solution therein.

4. An article according to claim 1 wherein the oxygen barrier of the second container comprises aluminum foil.

5. An article according to claim 1 wherein the second container is a sealed plastic pouch.

6. An article according to claim 1 wherein the first container is a single unit dosage disposable collapsible enema polyethylene bottle with a dispensing tip adapted for rectal administration of the 5-ASA solution therein and the second container is a sealed plastic pouch.

7. An article according to claim 6 wherein the pouch is formed at least in part from aluminum foil.

8. An article according to claim 1 wherein the solution contains about 0.1 to 0.2% w/w bisulfite dissolved therein.

9. A suspension according to claim 1 wherein the bisulfite is present as potassium metabisulfite.

10. A suspension according to claim 1 wherein the solution contains an amount of floculating agent effective to stabilize the suspension against caking of the undissolved 5-aminosalicylic acid.

11. An article according to claim 10 wherein the floculating agent is a water gellable polyacrylic acid.

12. An article according to claim 1 wherein the solution contains an amount of a thickener effective to stabilize the suspension against settling of the undissolved 5-aminosalicylic acid therefrom.

13. An article according to claim 12 wherein the thickener is xanthan gum.

14. An article according to claim 6 wherein the solution contains on a w/w basis about 1.5–10% of 5-aminosalicylic acid, up to about 0.2% by weight of sodium bisulfite, an amount of floculating agent effective to stabilize the suspension against caking of the undissolved 5-aminosalicylic acid and an amount of a thickener effective to stabilize the suspension against settling of undissolved 5-aminosalicylic acid therefrom.

15. An article according to claim 14 wherein the pouch is formed at least in part from aluminum foil.

16. A method of protecting a substantially colorless aqueous solution of substantially pure 5-ASA from decomposition and color formation therein upon prolonged storage, which comprises the steps of:
(a) maintaining the solution during storage in the presence dissolved therein of an amount of bisulfite effective only to protect the 5-ASA against decomposition and color formation resulting from reaction of the 5-ASA with a trace amount of atmospheric oxygen present prior to storage but ineffective to protect against atmospheric oxygen transmitted to the solution during storage;
(b) storing the solution in a sealed container which contains therein no more than a trace amount of atmospheric oxygen; and
(c) protecting the solution from contact with atmospheric oxygen during storage.

17. A method according to claim 16 wherein the sealed container is a plastic bottle or pouch in the form of a single unit dosage disposable collapsible enema bottle with a dispensing tip adapted for rectal administration of the 5-ASA solution therein and the solution contained therein is adapted for rectal administration and contains undissolved substantially pure 5-ASA suspended therein.

18. A method according to claim 17 wherein the plastic bottle is formed of a plastic having a substantial oxygen transmission rate and the 5-ASA solution is protected from contact with atmospheric oxygen during storage by a sealed second container in which the plastic bottle is stored and which is formed of a material having an oxygen transmission rate substantially lower than the plastic bottle.

19. A method according to claim 18 wherein the second sealed container is a pouch formed of a plastic laminate comprising aluminum foil.

20. A method according to claim 17 wherein the sealed container in which the solution is stored is a plastic bottle or pouch formed of a material having an oxygen transmission rate low enough to protect the solution against atmospheric oxygen being transmitted thereto during storage.

* * * * *